United States Patent
Khachaturov

(10) Patent No.: US 9,031,370 B2
(45) Date of Patent: May 12, 2015

(54) GROOVED OPTICAL FIBER JACKET

(71) Applicant: Lumenis Ltd., Yokneam Ilit (IL)

(72) Inventor: Arkady Khachaturov, Haifa (IL)

(73) Assignee: Lumenis Ltd. (IL)

( * ) Notice: Subject to any disclaimer, the term of this patent is extended or adjusted under 35 U.S.C. 154(b) by 0 days.

(21) Appl. No.: 14/196,865

(22) Filed: Mar. 4, 2014

(65) Prior Publication Data

US 2014/0254996 A1 Sep. 11, 2014

Related U.S. Application Data

(60) Provisional application No. 61/772,551, filed on Mar. 5, 2013.

(51) Int. Cl.
*G02B 6/02* (2006.01)
*A61B 18/22* (2006.01)

(52) U.S. Cl.
CPC ............. *A61B 18/22* (2013.01); *G02B 6/02395* (2013.01); *A61B 2018/2205* (2013.01); *A61B 2018/2244* (2013.01)

(58) Field of Classification Search
USPC .................................................. 385/123, 147
See application file for complete search history.

(56) References Cited

U.S. PATENT DOCUMENTS

| | | | |
|---|---|---|---|
| 4,381,140 A | * | 4/1983 | van der Hoek et al. ........ 385/104 |
| 5,714,196 A | * | 2/1998 | Vacha ............................ 427/154 |
| 2007/0171958 A1 | * | 7/2007 | Hoang et al. .................... 374/161 |
| 2007/0248307 A1 | * | 10/2007 | Page et al. ...................... 385/123 |
| 2010/0127034 A1 | * | 5/2010 | Bouchard et al. .................. 225/2 |
| 2013/0121656 A1 | * | 5/2013 | Chen et al. ..................... 385/135 |

* cited by examiner

*Primary Examiner* — Eric Wong
(74) *Attorney, Agent, or Firm* — Isus Intellectual Property PLLC

(57) ABSTRACT

An optical fiber is disclosed which includes a protective outer jacket. The outer protective jacket is grooved to include one or more peripheral grooves formed into the jacket. In operation of a laser device, laser energy passes through the optical fiber to the distal tip of the optical fiber. As the distal tip erodes, the outer protective jacket also erodes in a controlled fashion such that portions of the outer jacket flake off as the fiber tip erodes to the position of the peripheral grooves formed in the outer jacket rather than in a random fashion.

9 Claims, 2 Drawing Sheets

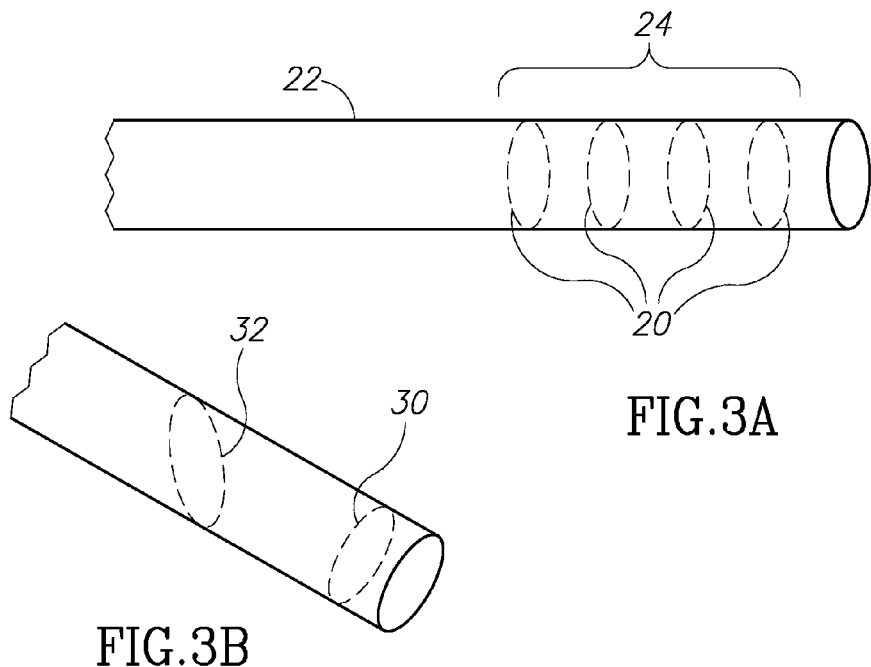
FIG.3A
FIG.3B
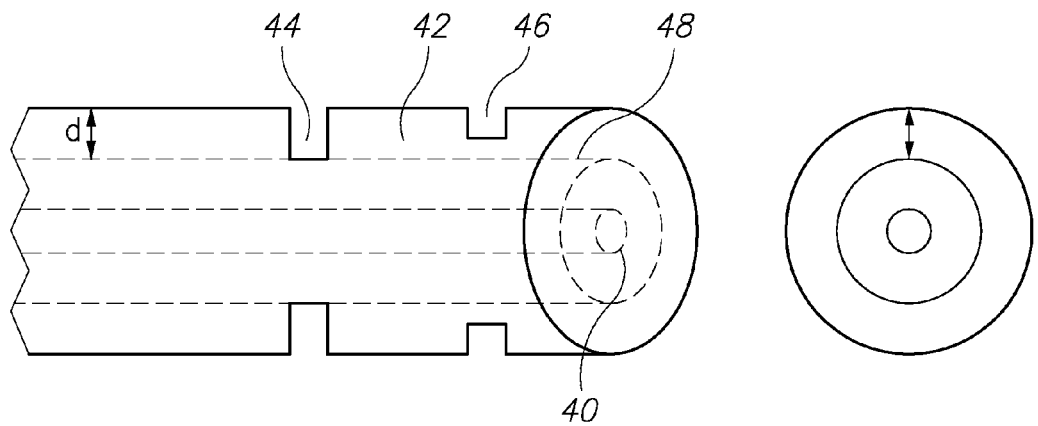
FIG.3C
FIG.3D
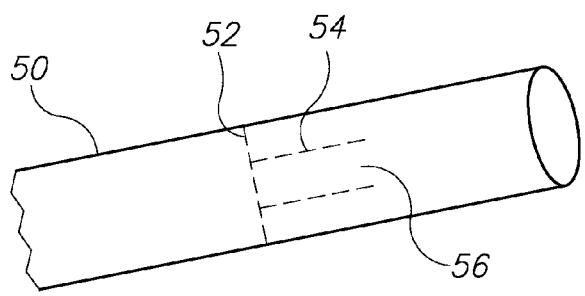
FIG.3E

GROOVED OPTICAL FIBER JACKET

RELATED APPLICATIONS

This application relates to and claims priority to U.S. Provisional Application Ser. No. 61/772,551, filed 5 Mar. 2013, the entire disclosure of which is herein incorporated by reference.

FIELD OF THE INVENTION

This application relates to optical fibers for medical laser devices and in particular to coverings or jackets for such optical fibers and improvements in such jackets to enhance their ability to rupture and self-destruct when in operation.

BACKGROUND OF THE INVENTION

Optical energy which is produced by medical lasers is often delivered to a target tissue through the use of an optical fiber or flexible hollow waveguide. A wide variety of medical lasers with appropriate delivery systems are known and used for wide spectrum of treatments, including kidney stone or other stone disintegration, tissue ablation, and tissue coagulation, the way of example only. However, optical fibers and waveguides tend to be fragile and requires some degree of the mechanical support. This usually involves the placement of a polymeric, Teflon or other suitable material jacket covering and surrounding the optical fiber to provide such support.

Moreover, an optical fiber or waveguide consists of a concentric core element surrounded by one or more layers of cladding materials. In some cases, the core element may be a silica core or simply a hollow waveguide. The cladding material in a hollow waveguide may be silver or other internal coating while, in the case of an optical fiber, such cladding material may be a transparent solid material. A polymeric jacket may have an appropriate optical characteristic to serve not only as a protection for the cladding element but also serve as a secondary cladding material in addition to its mechanical support purposes.

During treatment, in which laser energy is passed through an optical fiber or waveguide's proximal end, the laser beam energy will exit from the distal tip of for example, the optical fiber. This distal tip will tend to become eroded during laser treatment due to the intensity of the laser's power. This is because in medical treatment such as ablation treatments or treatments in which the laser is used to disintegrate or break up for example kidney stones, the higher level of energies and fluence which are delivered through the optical fiber and the interference of tissue or stone fragments tend to cause erosion and disintegration of the fiber tip. This tip erosion is known to affect mainly the fiber core, the cladding materials, and, as mentioned, the fiber tip. Due to the materials and structure of the jacketing material there is less proportionate erosion of the jacketing materials.

During operation, as the distal tip of the fiber erodes and diminishes in length, the jacket itself tends not to erode, as mentioned above, at the same rate. FIGS. 1A and 1B illustrate this phenomena. As can be seen in FIG. 1A, whereas the fiber tip 1 has eroded there is little erosion in the jacket material 2. Since, in a number of procedures, it is necessary or at least desirable to place the fiber tip against the bodily material that is to be ablated, it can be seen in FIG. 1A that the remaining jacket material prevents such contact. In addition, as can be seen in FIG. 1B, the jacket material 4, due in part to heating from the laser beam energy, may become jagged and may further make it difficult to contact the bodily material to be ablated. Another disadvantage is that the field of vision may be limited. Finally, when the jacketing material those fragment and separate from the remainder of the optical fiber and jacket combination, fragments which have separated may be large enough to interrupt the optical path of the laser beam, further complicating the medical procedure.

Thus, what is needed is an optical fiber jacket which eliminates the problems described above yet which provides an orderly destruction, erosion or disintegration of the optical fiber jacket more in synchronization with the erosion of the optical fiber tip itself.

BRIEF DESCRIPTION OF THE DRAWINGS

FIGS. 3A-3E illustrate a number of embodiments of the present invention.

DETAILED DESCRIPTION OF THE PRESENT INVENTION

Turning now to FIGS. 2A, 2B, and 3A-3E, these figures illustrate one or more aspects of the present invention. The present invention incorporates one or more peripheral grooves into the outer jacket material. These peripheral grooves may totally encompass or only partially encompass the periphery of the jacking material. The grooves may be a single groove or number of grooves, and the distance between grooves may be selected to place such grooves close to or far apart from one another. The depth of the grooves may also vary. The jacket, as mentioned above, may be either a polyimide, Teflon or other suitable material and generally has uniform thickness along the optical fiber waveguide. In one or more aspects of the present invention, the depth of the groove or grooves may be: less than the jacket thickness itself, be nearly the thickness of the jacket, or even equal to or exceed the thickness of the jacket itself.

Figure 1A:
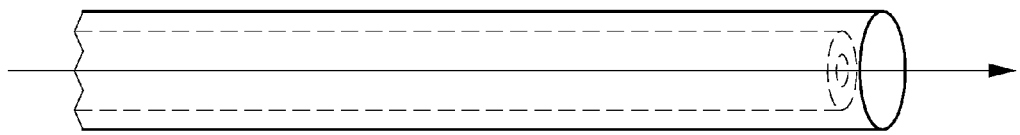
FIGS. 1A and 1B illustrate prior art jacketed optical fibers and their shortcomings.
Figure 1B:
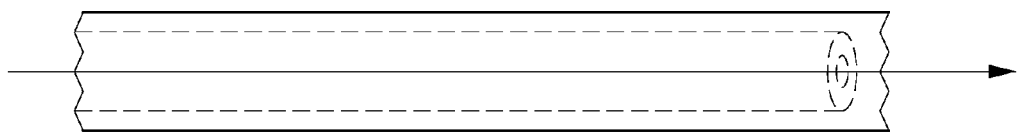
Figure 2A:
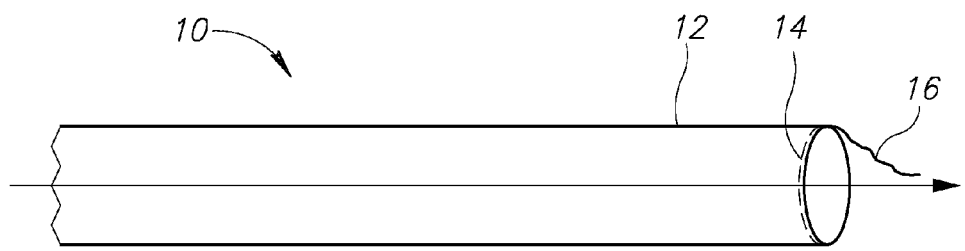
FIGS. 2A and 2B illustrate jacket problems associated with prior art devices.
Figure 2B:
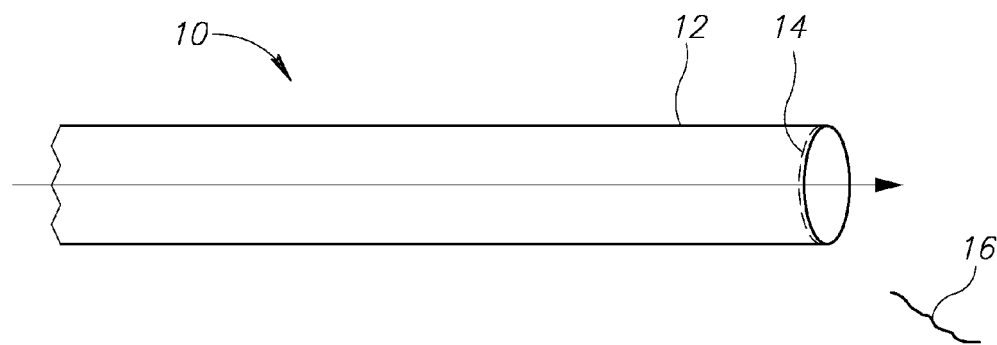

FIGS. 2A and 2B illustrate an optical fiber in an embodiment which includes a peripheral groove 14 in the jacket material of the present invention. While a single groove 14 is illustrated, it is understood that multiple grooves may be incorporated. As illustrated in FIG. 2A, the distal tip of the optical fiber has deteriorated to a position in which the peripheral groove 14 is almost reached. In FIG. 2B, the deterioration is to a position in which the peripheral groove 14 has been reached. In FIG. 2A, an optical fiber 10 has a jacket material 12 into which is incised a peripheral groove 14. As shown in FIG. 2A, this figure illustrates the environment on the assumption that the laser beam has been activated and that the fiber tip has eroded more than the jacket itself. Excess jacket surplus 16 is shown as remaining attached to the optical fiber, and, as illustrated, may interfere with the operation of the laser beam since the axis jacket material is shown as partially obstructing the optical fiber path. FIG. 2B illustrates the operation of the peripheral groove 14 once the optical fiber tip has eroded to the position of the peripheral groove 14. The weakness introduced by grooving the jacket causes the jacket material 16 to separate from the optical fiber itself in a controlled manner. Previously, without the peripheral groove(s) of the present invention, the breakaway of the excess jacket material was uncontrolled and somewhat random, increasing the likelihood of interference with the operation of the laser beam due to the presence of jacket material in the optical path of the laser beam. Thus, as can be seen in FIG. 2B, the excess jacket material does not interfere with the optical fiber path so that the medical procedure may proceed without such interference. According to an aspect of the present invention, the peripheral groove lines may create weaker peripheral lines such that the jacket is more easily breakable and tends to yield under mechanical and thermal strains imposed by the operation of the laser beam through the optical fiber. As a result, the excess surplus of jacket material will simply tear off at the peripheral lines and avoid further interaction with the laser beam which, as mentioned, may negatively affect the efficiency of the laser treatment.

FIGS. 3A through 3D illustrate various implementations of peripheral grooves in an optical fiber. In FIG. 3A, for example, a plurality of grooves 20 are shown formed into the jacket material 22. The distance between the peripheral grooves may be selected according to the material of the jacket, the type and power of the laser beam, such other criteria such as the material of the optical fiber itself. Clearly, if it is desired that there be smaller portions of jacketing material dislodges, the peripheral grooves may be spaced closer to one another. This may be desirable because in a number of medical procedures involving the use of lasers and optical fibers, the volume around the bodily material to be ablated may be surrounded by a fluid material. In such cases, when a portion of jacketing material is dislodged, it will tend to float around in the fluid material and may interfere with the laser beam attempting to contact and ablate the bodily material. Smaller pieces of jacketing material will tend to be less interfering with the application of the laser beam.

FIG. 3B illustrates two types of groove shapes or configurations. These include a circular shaped groove 30 and an elliptically shaped groove 32. Other shapes or configurations may also be used so long as the group structure is such that it tends to break apart as the erosion of the tip approaches or nearly approaches the grooves. The grooves may be formed only in the distal portion of the optical fiber or in other portions as well.

FIG. 3C illustrates an optical fiber 40 which has surrounding it a jacket 42. Into the jacket 42, one or more grooves 44 and 46 may be formed into the jacket 42. The groove depth may be the depth of the jacket itself as shown in 42 or may be less than the depth of the jacket shown in 46. Grooves of the type shown in 44 and 46 may be used alternatively such that, by way of example only, thy groove of the type 44 may alternate with grooves of type 46 and a desired sequence or organization. As shown in FIG. 3C, groove 44 reaches down to the cladding 48 itself. This is also shown in FIG. 3D.

FIG. 3E illustrates yet another embodiment of the present invention. In FIG. 3E, the outer jacket 50 is formed with not only one or more circular shaped grooves 52 but also grooves 54 formed in a direction along the optical axis of the optical fiber and in contact with the one or more circular shaped grooves 52. In this embodiment, the longitudinal sections 56 formed in the jacket will tend to "splay" away from the optical fiber tip once the optical fiber tip has been eroded to the distal portion of the longitudinal sections 56. The portions 56 move away from the periphery of the optical fiber and tend not to interfere with the operation of the optical fiber tip. Once the optical fiber tip has eroded to the level the peripheral groove 52, the longitudinal portions 56 will tend to break away entirely from the jacket 50.

According to another aspect of the present invention, a method is disclosed using optical fibers for a medical laser procedure. This method includes forming one or more peripheral grooves towards the distal end of an optical fiber waveguide into the jacketing material prior to the medical laser procedure. The method may further include using an adjusted fiber stripper or cleaver which is designed to create the peripheral grooves into an optical fiber or waveguide jacketing material. These grooves may partially or totally penetrate the thickness of the jacketing material.

In order to form a peripheral grooves into the jacketing material of the types described above, a number of different modalities may be utilized. For example, a wire stripper of known construction may be utilized to cut through the desired amount of jacketing material without compromising the cladding material surrounding the optical fiber or compromising the optical fiber itself. Known wire strippers will strip the insulation off of wires and have adjustable penetration depths that may be set using a plurality of cutting faces. Such a device may create one for more grooves simultaneously. According to another aspect of the invention, the one or more peripheral grooves may be created by a single punch of the stripper. In yet another aspect of the invention such a device may create one or more grooves by a punching movement followed by rotation movement so that the full circumference of the outer jacket, at the point of grooving, is fully encompassed. Such a rotation movement may require rotating the device at an angle which is a function of the number of proving elements in the device. For example one type of grooving teeth may require almost or all of a 360° rotation, while two opposite teeth may perform the same function using only a 180° rotation.

Although the particular embodiments shown and described above will prove to be useful in many medical procedures involving the use of jacketed laser fibers to which the present invention pertains, further modifications of the present invention will occur to persons skilled in the art. All such modifications are deemed to be within the scope and spirit of the present invention as defined by the appended claims.

What is claimed is:

1. An optical fiber having an optical fiber core, a surrounding cladding layer and a jacketing layer of a given thickness surrounding the cladding layer, the optical fiber comprising:
   the optical fiber core being of a material suitable for conveying one or more of ablative, coagulating or disintegrating laser energy from a medical treatment laser to a tip of the optical fiber core and to human body portions;
   the optical fiber core being of a material in which the tip erodes when the laser energy is conveyed from the medical treatment laser to the tip of the optical fiber core;
   the jacketing layer being of a material which erodes less than the tip of the optical fiber core when the laser energy is conveyed from the medical treatment laser to the tip of the optical fiber; and
   one or more peripheral grooves formed in the jacketing layer, the one or more peripheral grooves segmenting the jacketing layer, and wherein portions of the jacketing layer segment and break off from the jacketing layer upon the application of the laser energy through the optical fiber to the tip of the optical fiber core.

2. The optical fiber of claim 1 wherein the one or more peripheral grooves are formed in the entirety of the circumference of the jacketing material.

3. The optical fiber of claim 1 wherein the depth of the one or more peripheral grooves is one of: less than the given thickness of the jacketing material and equal to the given thickness of the jacketing material.

4. The optical fiber of claim 1 wherein the one or more peripheral grooves are in the form of circular grooves.

5. The optical fiber of claim 1 wherein the one or more peripheral groves are in an elliptical form.

6. The optical fiber of claim 1, further comprising one or more longitudinal grooves along the optical axis of the optical fiber, the one or more longitudinal grooves being in contact with at least one circular peripheral groove.

7. The optical fiber of claim 1, wherein the one or more peripheral groves comprise a plurality of peripheral grooves spaced from one another to provide a given density of grooves per unit length along the optical fiber.

8. The optical fiber of claim 1, wherein the jacketing material comprises one or more of: a polyimide or Teflon.

9. The optical fiber of claim 1, wherein the medical treatment laser is directed at body portions comprising one or more of: kidney stone disintegration, non-kidney stone disintegration; tissue ablation and tissue coagulation.

* * * * *